(12) United States Patent
Cannon et al.

(10) Patent No.: US 11,497,475 B2
(45) Date of Patent: Nov. 15, 2022

(54) ULTRASOUND IMAGE ACQUISITION OPTIMIZATION ACCORDING TO DIFFERENT RESPIRATION MODES

(71) Applicant: Caption Health, Inc., Brisbane, CA (US)

(72) Inventors: Michael G. Cannon, Haverford, PA (US); Nicolas Poilvert, Seattle, WA (US); Charles Cadieu, Menlo Park, CA (US); Ha Hong, San Ramon, CA (US); Kilian Koepsell, San Francisco, CA (US); Ali Chaudhry, San Francisco, CA (US); Nripesh Parajuli, San Mateo, CA (US)

(73) Assignee: Caption Health, Inc., Brisbane, CA (US)

( * ) Notice: Subject to any disclaimer, the term of this patent is extended or adjusted under 35 U.S.C. 154(b) by 0 days.

(21) Appl. No.: 16/778,605

(22) Filed: Jan. 31, 2020

(65) Prior Publication Data

US 2021/0236094 A1     Aug. 5, 2021

(51) Int. Cl.
*A61B 8/08*     (2006.01)
*A61B 5/08*     (2006.01)
*A61B 5/085*    (2006.01)

(52) U.S. Cl.
CPC .......... *A61B 8/5207* (2013.01); *A61B 5/0816* (2013.01); *A61B 8/5215* (2013.01); *A61B 5/085* (2013.01)

(58) Field of Classification Search
CPC ... A61B 8/5207; A61B 5/0816; A61B 8/5215; A61B 5/085; A61B 8/5276;
(Continued)

(56) References Cited

U.S. PATENT DOCUMENTS

| 7,769,430 B2* | 8/2010 | Mostafavi | A61B 6/541 600/428 |
| 7,778,691 B2* | 8/2010 | Zhang | A61B 5/1135 600/427 |

(Continued)

OTHER PUBLICATIONS

Liu Menghan, et al., "Asthma Pattern Identification via Continuous Diaphragm Motion Monitoring," IEEE, vol. 1, No. 2, Jun. 1, 2015.
(Continued)

*Primary Examiner* — Oommen Jacob
(74) *Attorney, Agent, or Firm* — Wilson Sonsini Goodrich & Rosati

(57) ABSTRACT

Embodiments of the present invention provide a method, system and computer program product for ultrasound image acquisition optimization according to different respiration modes. A method for ultrasound image acquisition optimization according to different respiration modes includes acquiring by an ultrasound imaging device, an ultrasound image of a target organ. The method further includes comparing attributes of the acquired ultrasound image to association data in a data store of associations associating attributes of previously acquired ultrasound imagery of different images of the target organ with different modes of respiration. Finally, the method includes determining from the comparison, a mode of respiration evident from the acquired ultrasound image and presenting the determined mode in the ultrasound imaging device.

15 Claims, 2 Drawing Sheets

(58) Field of Classification Search
CPC ....... A61B 8/5261; A61B 8/4477; A61B 8/08;
A61B 8/5223; A61B 8/5292; A61B
6/5247; A61B 8/4416; A61B 8/483; A61B
8/543; A61B 2090/365; A61B 2090/378;
A61B 2017/00699; A61B 6/032; A61B
5/08; A61B 5/1135; A61B 6/541; A61B
5/087; A61N 7/02; A61N 2005/1061;
A61N 2005/1058; A61N 5/1048; A61N
5/1037; A61N 5/1064; A61N 5/1042;
G16H 50/30
See application file for complete search history.

(56) References Cited

U.S. PATENT DOCUMENTS

| | | | |
|---|---|---|---|
| 2002/0143246 A1* | 10/2002 | Hardy | G01R 33/56308 600/410 |
| 2004/0005088 A1* | 1/2004 | Jeung | A61N 5/1049 382/128 |
| 2005/0074154 A1* | 4/2005 | Georgescu | G06T 7/20 382/128 |
| 2005/0215904 A1 | 9/2005 | Sumanaweera et al. | |
| 2008/0144770 A1* | 6/2008 | Lee | A61N 5/1049 378/65 |
| 2008/0144908 A1* | 6/2008 | West | A61N 5/1031 382/131 |
| 2014/0316247 A1* | 10/2014 | Hwang | A61N 7/02 600/411 |
| 2015/0371379 A1 | 12/2015 | Averikou et al. | |
| 2017/0020489 A1* | 1/2017 | Kang | A61B 8/4245 |
| 2018/0137244 A1* | 5/2018 | Sorenson | G16H 30/20 |
| 2019/0219647 A1 | 7/2019 | Foo et al. | |
| 2021/0236094 A1* | 8/2021 | Cannon | A61B 8/54 |

OTHER PUBLICATIONS

Kulhare, et al., "Ultrasound-Based Detection of Lung Abnormalities Using Single Shot Detection Convolutional Neural Networks," 5th Int. Workshop MSM, Sep. 15, 2018.
Ji Zhang, et al., "Fast Algorithm for Respiratory Motion Correction in Free-Breathing Contrast-Enhanced Ultrasound Imaging," SPIE, vol. 7968, Dec. 31, 2011.
Ginghina, et al., "Respiratory Maeuvers in Echocardiography: A Review of Clinical Applications," Cardiovascular Ultrasound, Aug. 26, 2009.
Al-Biltagi, et al., "Doppler Echocardiographic Changes in Respiratory Diseases," InTech, Jul. 2011.
United Kingdom Patent Application No. 2101234.9 Combined Search and Examination Report dated Nov. 24, 2021.

* cited by examiner

ULTRASOUND IMAGE ACQUISITION OPTIMIZATION ACCORDING TO DIFFERENT RESPIRATION MODES

BACKGROUND OF THE INVENTION

Field of the Invention

The present invention relates to ultrasound imaging and more particularly to ultrasound image acquisition.

Description of the Related Art

Ultrasound imaging, also known as sonography, is a medical imaging technique that employs high-frequency sound waves to view three-dimensional structures inside the body of a living being. Because ultrasound images are captured in real-time, ultrasound images also show movement of the internal organs of the body as well as blood flowing through the blood vessels of the human body and the stiffness of tissue. Unlike x-ray imaging, ultrasound imaging does not involve ionizing radiation thereby allowing prolonged usage of ultrasound imaging without threatening tissue and internal organ damage from prolonged radiation exposure.

To acquire ultrasound imagery, during an ultrasound exam, a transducer, commonly referred to as a probe, is placed directly on the skin or inside a body opening. The probe is coupled to image generation circuitry that includes circuitry adapted to transmit and receive signals to and from the probe, and may include a beamformer, though synthetic aperture imaging systems may use retrospective image formation reducing the need for beamforming and scan conversion functions. A thin layer of gel is applied to the skin so that the ultrasound waves are transmitted from the probe through the medium of the gel into the body. The ultrasound image is produced based upon a measurement of the reflection of the ultrasound waves off the body structures. The strength of the ultrasound signal, measured as the amplitude of the detected sound wave reflection, and the time taken for the sound wave to travel through the body provide the information necessary to compute an image of target structures of the body. As well, the "Doppler" effect may be used in ultrasound imagery to measure the velocity and direction of fluid flow within the structures of the body (namely, blood) as well as the velocity and direction of moving tissue such as heart muscle or valves Compared to other prominent methods of medical imaging, ultrasound presents several advantages to the diagnostician and patient. First and foremost, ultrasound imaging provides images in real-time. As well, ultrasound imaging requires equipment that is portable and can be brought to the bedside of the patient. Further, as a practical matter, the ultrasound imaging equipment is substantially lower in cost than other medical imaging equipment, and as noted, does not use harmful ionizing radiation. Even still, ultrasound imagery is not without challenge.

In this regard, unlike most other diagnostic imaging modalities, such as x-ray, magnetic resonance imaging (MRI), computed tomography (CT), and the like, ultrasound imaging depends upon the careful and dynamic manipulation of a handheld transducer applied to the patient. For good results, this scanning process requires highly trained and skilled users. These users must learn how to adjust the position and angle of the transducer on the patient in order to obtain usable images. These users further must know how to position the patient for different clinical applications and targets. Yet, this positioning can be challenging and often must change in both gross ways and also subtle ways during the examination in order to achieve an acceptable view for use in medical diagnoses.

Adjunct to positioning, for a large number of clinical applications, the respiration of the subject to ultrasound scanning can play a key role in the quality of an acquired ultrasound image. To wit, respiration can affect ultrasound image in so far as a significant impedance mismatch exists between soft tissue and air in the body. As it is well known, air in the ultrasound path is a strong reflector that prevents transmission of ultrasound waves and creates reverberation artifacts. This effect can be most noted in anatomical targets adjacent to the lungs, though it can be seen in other places, such as in the bowel where bowel gas occurs. In targets near the lungs, the expansion and contraction of the lungs during breathing can move air in and out of the ultrasound beam path, causing interference that follows the respiratory cycle. Another effect of this is that a target organ, such as the heart, will move in relation to the respiratory cycle, as the expansion and contraction of the lungs pushes or pulls the heart into different positions. This can cause a target to move in and out of the ultrasound beam such that it is impossible to properly visualize the target. This effect can be a problem even if breathing does not directly put air in the ultrasound path.

BRIEF SUMMARY OF THE INVENTION

Embodiments of the present invention address deficiencies of the art in respect to ultrasound imaging and provide a novel and non-obvious method, system and computer program product for ultrasound image acquisition optimization according to different respiration modes. In an embodiment of the invention, a method for ultrasound image acquisition optimization according to different respiration modes includes acquiring by an ultrasound imaging device, one or more ultrasound images of a target organ. The method further includes comparing attributes of the acquired ultrasound imagery to association data in a data store of attributes that associate previously acquired ultrasound imagery of different images of the target organ with different modes of respiration. Finally, the method includes determining from the comparison, a mode of respiration evident from the acquired ultrasound image and presenting the determined mode in the ultrasound imaging device, for instance by way of a visual display of the mode in a display of the imaging device, by audible methods or even tactile methods. Of importance, the determination is based upon the comparison attributes of the acquired ultrasound imagery and not upon an external physiological signal input providing data regarding respiration.

In one aspect of the embodiment, the data store of associations is a deep neural network trained to associate different modes of respiration with corresponding previously acquired ultrasound imagery of the different images of the target organ. As such, the neural network may be presented with the acquired ultrasound image and may return a probability of a correlation between the acquired ultrasound image and a particular mode of respiration. In another aspect of the embodiment, the data store of associations is a table associating individual different images to corresponding the modes of respiration. As such, pixel-wise image comparison may be performed in order to produce a particular mode of respiration assigned to a highest percent-wise matching image in the data store.

In yet another aspect of the embodiment, the method additionally includes determining a quality of the acquired ultrasound image, identifying a change in the determined mode of respiration correlated with an improvement in quality of ultrasound imagery of the target organ and presenting the change in the determined mode in the display of the ultrasound image acquisition device. In even yet another aspect of the embodiment, the method additionally includes determining a physiological condition, such as a prospective abnormality or disease, from the acquired ultrasound image, identifying a change in the determined mode of respiration correlated with an improvement in quality of ultrasound imagery of the target organ for diagnosing the prospective abnormality or disease and presenting the change in the determined mode in the ultrasound image acquisition device. In this regard, the change can be presented visually in a display of the device, audibly from a speaker of the device, or tactilely in a probe of the device.

In another embodiment of the invention, a data processing system is configured for ultrasound image acquisition optimization according to different respiration modes. The system includes a computer with memory and at least one processor, a display coupled to the computer, image generation circuitry coupled both to the computer and also to the display, and an ultrasound imaging probe that has a transducer connected to the image generation circuitry. The system further includes an ultrasound image acquisition optimization module executing in the memory of the computer. The module includes program code enabled upon execution by the processor of the computer to acquire by an ultrasound imaging device, one or more ultrasound images of a target organ, compare attributes of the acquired ultrasound image to data in a data store that associates attributes of previously acquired ultrasound imagery of different images of the target organ with different modes of respiration, determine from the comparison, a mode of respiration evident from the acquired ultrasound image and present the determined mode in the ultrasound imaging device.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for ultrasound image acquisition optimization according to different respiration modes. In accordance with an embodiment of the invention, different images of different organs are associated with different modes of respiration including inhalation and exhalation in a data store of associations. In this regard, the data store of associations can be an image table correlating different images with different modes of respirations, or a deep neural network trained to associate each of the different images with corresponding ones of the different modes of respiration.

Thereafter, an ultrasound imaging device acquires ultrasound imagery for a target organ and compares characteristics of the different images to the data store of associations in order to determine a mode of respiration for the acquired imagery. The mode of respiration is then presented in the ultrasound imaging device in order to assist an operator of the ultrasound imaging device in acquiring suitable imagery of the target organ. Optionally, a quality of the acquired image is determined along with a change in mode of respiration previously associated with an improvement in quality of an image of the target image. Consequently, the change in mode of respiration may be presented as a guidance signal in the device such as a visual cue in a display of the device, an audible cue presented by the device, or a tactile view transmitted by the device to the probe of the device, in order to assist an operator of the ultrasound imaging device in acquiring suitable imagery of the target organ.

Figure 1:
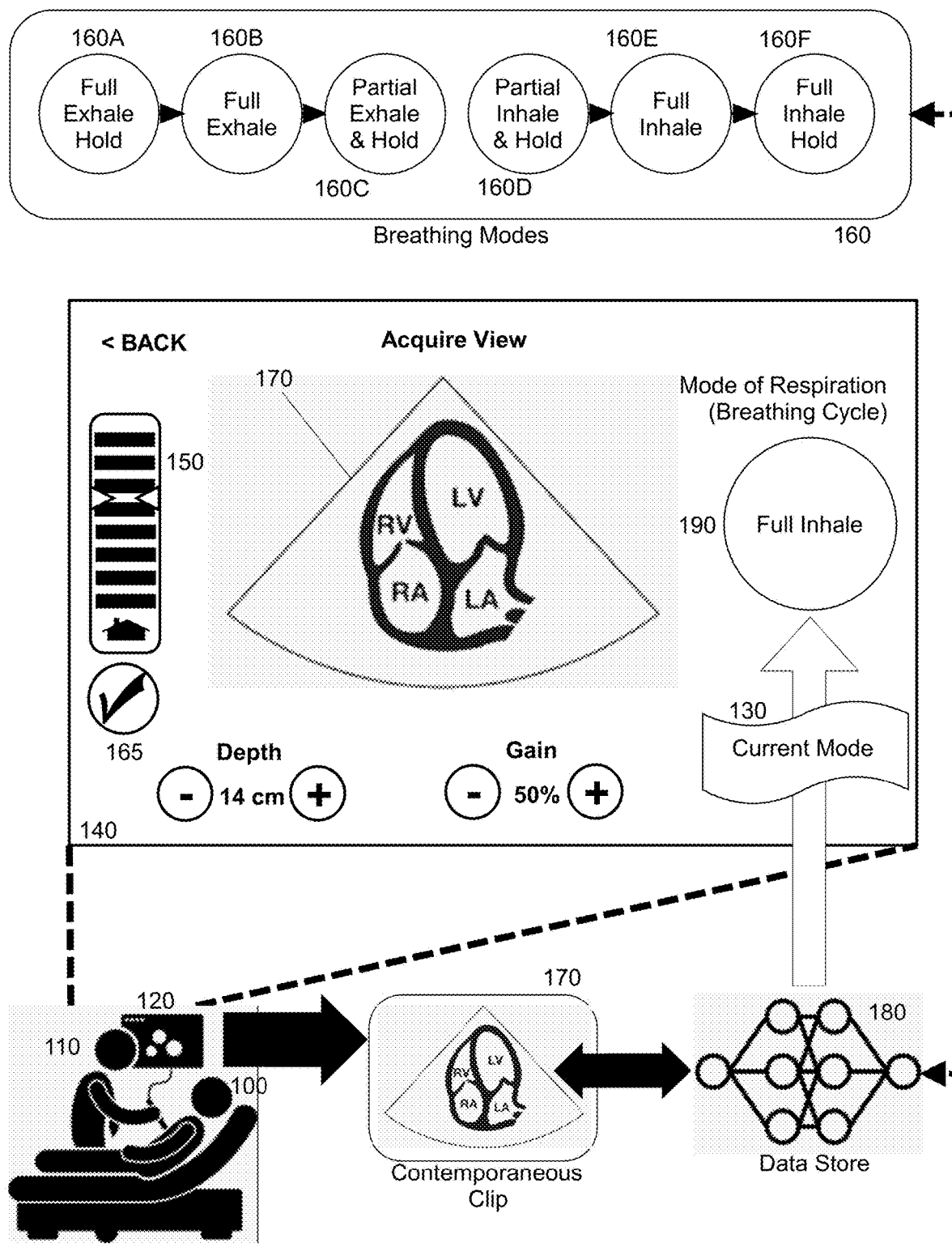
FIG. 1 is a pictorial illustration of a process for ultrasound image acquisition optimization according to different respiration modes.

In further illustration, FIG. 1 pictorially shows a process for ultrasound image acquisition optimization according to different respiration modes. As shown in FIG. 1, an ultrasound operator 110 manipulates an ultrasound imaging system 120 to acquire ultrasound imagery 170 of a target organ of a patient 100. A display 140 of the ultrasound imaging system 120 provides guidance feedback to the ultrasound operator 110. In particular, a quality meter 150 is disposed in the display 140 and indicates a sliding scale of quality of the acquired ultrasound imagery 170 relative to a known view sought to be acquired for the target organ. For example, in connection with the imaging of a heart, the known view may include a parasternal long axis view, a parasternal short axis view, an apical two, three, four or five chamber view or a subcostal view. To the extent that the acquired ultrasound imagery 170 is determined to have a corresponding quality value that meets or exceeds a threshold quality for the specified view, a success icon 165 is displayed in connection with the quality meter 150 and the acquired ultrasound imagery 170 is displayed in a window as a most recently acquired video clip of satisfactory quality.

During acquisition of the acquired ultrasound imagery 170, attributes of the acquired ultrasound imagery 170 are compared to attributes of prior imagery disposed within a data store 180 and associated with different modes of breathing 160 within the breathing cycle. In this regard, the different modes of breathing 160 range from a full exhalation while preventing an inhalation 160A, to a full inhalation while preventing an exhalation 160F, and intermediate modes including full exhalation 160B, a partial exhalation while inhibiting further inhalation or exhalation 160C, a partial inhalation while inhibiting further inhalation or exhalation 160D, and a full inhalation 160E. Optionally, the data store 180 is a table of imagery and associated breathing modes so that a pixel-wise comparison of the acquired ultrasound imagery 170 to the images in the table in order to identify enough commonality of pixels as to content-based match the acquired ultrasound imagery 170 to an image in the table associated with a particular one of the breathing modes 160. Alternatively, the data store 180 is a convolutional neural network trained with different imagery annotated with different ones of the breathing modes 160. But, in either circumstance, based upon the comparison, a current mode 130 of breathing is identified amongst the different modes of breathing 160 in response to a submission of the acquired ultrasound imagery 170 to the data store 180.

Figure 2:
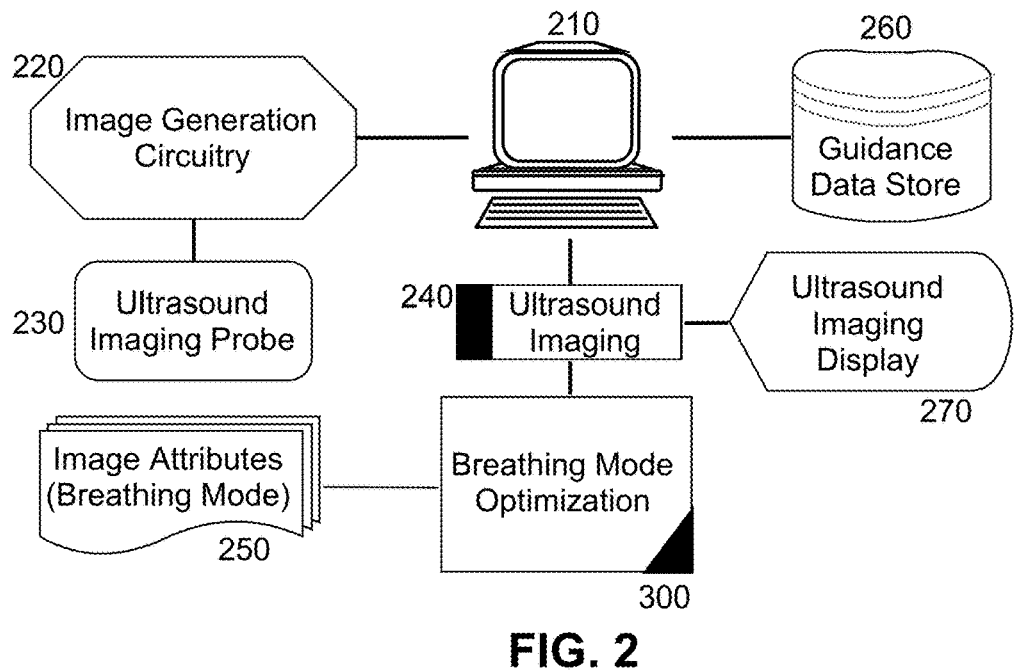
FIG. 2 is a schematic illustration of a data processing system adapted for ultrasound image acquisition optimization according to different respiration modes; and, FIG. 3 is a flow chart illustrating a process for ultrasound image acquisition optimization according to different respiration modes.

The process described in connection with FIG. 1 may be implemented within a data processing system. In further illustration, FIG. 2 schematically illustrates a data processing system adapted for ultrasound image acquisition optimization according to different respiration modes. The system includes a host computing system 210 that includes a computer with at least one processor, memory and a display. The host computing system 210 also includes a data store 250. The host computing system 210 yet further is coupled to an ultrasound imaging system 220 adapted to store in memory, ultrasound imagery acquired through the placement of an imaging probe 230 proximate to a target organ of interest in a mammalian subject by operation of image generation circuitry 220.

Importantly, the host computing system 210 is communicatively coupled to fixed storage 260, either locally or remotely ("in the cloud") storing therein a neural network and a programmatic interface to the neural network. The neural network is trained to characterize one or more features of the target organ, for example an ejection fraction value of a heart, or the presence or absence of aortic stenosis. To do so, video clip imagery 270 of a specified view of the target organ acquired by the ultrasound imaging system 220 is provided to the neural network which in turn accesses the programmatic interface so that the neural network may then output the characterization for the video clip imagery along with an indication of confidence in that characterization. The ultrasound imaging system 220 in turn renders on the display of the host computing system 210 not only the video clip imagery 270, but also the characterization and optionally, the indication of confidence.

In accordance with an embodiment of the invention, a breathing mode optimization module 300 is included with the ultrasound imaging system 220. The module 300 includes computer program instructions enabled, upon execution in the host computing system 210, to compare the video clip imagery 270 to a data store of image attributes 250 that have been each correlated with a different mode of breathing. The data store of image attributes 250 may be a neural network trained with imagery of the target organ and annotated with different breathing modes. Upon correlating the video clip imagery 270 to a particular breathing mode, the program instructions present the breathing mode in the display of the ultrasound imaging system 220. Optionally, the program instructions interrogate the data store 260 to determine a quality of the video clip imagery 270 and to retrieve a specific breathing mode associated with an improvement in quality. As another option, the program instructions interrogate the data store 260 to identify a specific physiological condition evident in the video clip imagery 270 and to retrieve a specific breathing mode associated with an improvement in imaging the physiological condition. In either circumstance, the specific breathing mode is presented in the ultrasound imaging system 220, either visually, audibly or by tactile means (haptic feedback in the imaging wand 230).

Figure 3:
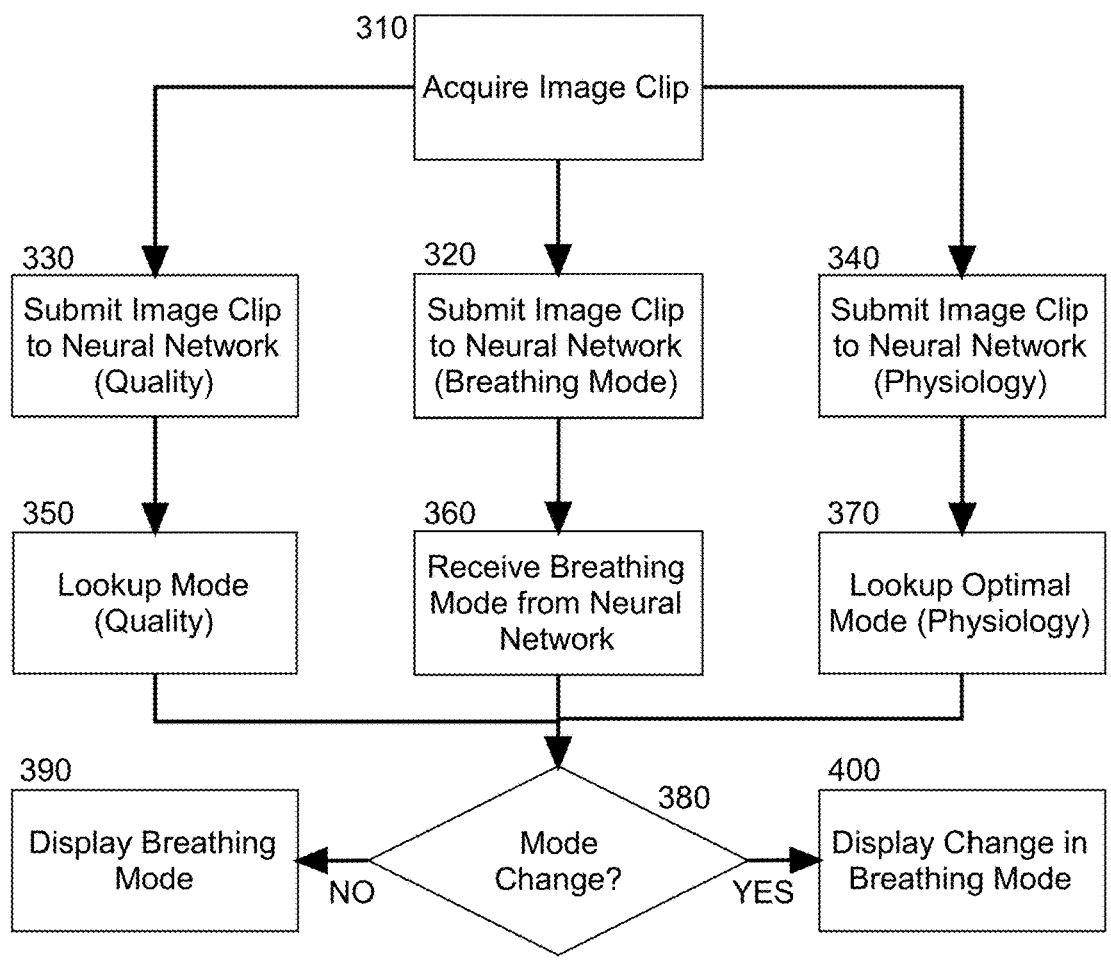

In even yet further illustration of the operation of the breathing mode optimization module 300, FIG. 3 is a flow chart illustrating a process for ultrasound image acquisition optimization according to different respiration modes. Beginning in block 310, an image clip of a target organ is acquired. In block 320 the image clip is submitted to a neural network trained to correlate specific ultrasound imagery of the target organ with a specific mode of breathing. As such, in block 360, the neural network returns a mode of breathing having a highest probability of association with the image clip acquired for the target organ. Concurrently, in block 330, the image clip is submitted to a neural network trained to correlate specific ultrasound imagery of the target organ with a specific image quality and in block 350, the neural network returns a particular quality having a highest probability of association with the image clip acquired for the target organ. Finally, in block 340, the image clip is submitted to a neural network trained to correlate specific ultrasound imagery of the target organ with a specific physiological condition and in block 370, the neural network returns a particular physiological condition having a highest probability of association with the image clip acquired for the target organ.

Then, in decision block 380, it is determined whether or not a breathing mode change is warranted in light of the specific image quality, the specific physiological condition, or both. If no breathing mode change is determined to be warranted, in block 390, the mode of breathing returned by the neural network is presented in the ultrasound imaging system for the benefit of the operator. But, in decision block 380, if a change in breathing mode is determined to be warranted, either based upon the specific quality, the particular physiological condition, in block 400 a change in breathing mode associated with either or both of the specific quality and particular physiological condition is presented in the ultrasound imaging system.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for ultrasound image acquisition optimization according to different respiration modes, the method comprising:
    acquiring by an ultrasound imaging device, one or more ultrasound images of a target organ;
    comparing attributes of the acquired ultrasound image to association data in a data store of associations associating attributes of previously acquired ultrasound imagery of different images of the target organ with different modes of respiration ranging from a full exhalation while preventing an inhalation, to a full inhalation while preventing an exhalation, and intermediate modes including full exhalation, a partial exhalation while inhibiting further inhalation or exhalation, a partial inhalation while inhibiting further inhalation or exhalation, and a full inhalation;
    determining from the comparison, a mode of respiration evident from the acquired ultrasound image;
    determining a quality of the acquired ultrasound image;
    identifying a change in the determined mode of respiration correlated with an improvement in quality of ultrasound imagery of the target organ; and,
    presenting the change in the determined mode in the ultrasound imaging device.

2. The method of claim 1, wherein the data store of associations is a deep neural network trained to associate different ones of the modes of respiration with corresponding ones of the previously acquired ultrasound imagery of the different images of the target organ.

3. The method of claim 1, wherein the data store of associations is a table associating individual ones of the different images to corresponding ones of the modes of respiration.

4. The method of claim 1, further comprising:
    determining a prospective physiological condition from the acquired ultrasound image;
    identifying a change in the determined mode of respiration correlated with an improvement in quality of ultrasound imagery of the target organ for diagnosing the physiological condition; and,
    presenting the change in the determined mode in the ultrasound image acquisition device.

5. The method of claim 1, wherein the determination is based upon the comparison attributes of the acquired ultrasound image and not upon an external physiological signal input providing data regarding respiration.

6. A data processing system configured for ultrasound image acquisition optimization according to different respiration modes, the system comprising:
    a computer with memory and at least one processor;
    a display coupled to the computer;

image generation circuitry coupled to the computer and the display;

an ultrasound imaging probe comprising a transducer connected to the image generation circuitry; and, an ultrasound image acquisition optimization module executing in the memory of the computer, the module comprising program code enabled upon execution by the processor of the computer to perform:

acquiring by an ultrasound imaging device, an ultrasound image of a target organ;

comparing attributes of the acquired ultrasound image to association data in a data store of associations associating attributes of previously acquired ultrasound imagery of different images of the target organ with different modes of respiration ranging from a full exhalation while preventing an inhalation, to a full inhalation while preventing an exhalation, and intermediate modes including full exhalation, a partial exhalation while inhibiting further inhalation or exhalation, a partial inhalation while inhibiting further inhalation or exhalation, and a full inhalation;

determining from the comparison, a mode of respiration evident from the acquired ultrasound image;

determining a quality of the acquired ultrasound image;

identifying a change in the determined mode of respiration correlated with an improvement in quality of ultrasound imagery of the target organ; and, presenting the change in the determined mode in the ultrasound aging device.

7. The system of claim 6, wherein the data store of associations is a deep neural network trained to associate different ones of the modes of respiration with corresponding ones of the previously acquired ultrasound imagery of the different images of the target organ.

8. The system of claim 6, wherein the data store of associations is a table associating individual ones of the different images to corresponding ones of the modes of respiration.

9. The system of claim 6, wherein the program code further performs:

determining a prospective disease from the acquired ultrasound image;

identifying a change in the determined mode of respiration correlated with an improvement in quality of ultrasound imagery of the target organ for diagnosing the prospective disease; and, presenting the change in the determined mode in the ultrasound image acquisition device.

10. The system of claim 6, wherein the determination is based upon the comparison attributes of the acquired ultrasound image and not upon an external physiological signal input providing data regarding respiration.

11. A computer program product for ultrasound image acquisition optimization according to different respiration modes, the computer program product including a non-transitory computer readable storage medium having program instructions embodied therewith, the program instructions executable by a device to cause the device to perform a method including:

acquiring by an ultrasound imaging device, an ultrasound image of a target organ;

comparing attributes of the acquired ultrasound image to association data in a data store of associations associating attributes of previously acquired ultrasound imagery of different images of the target organ with different modes of respiration ranging from a full exhalation while preventing an inhalation, to a full inhalation while preventing an exhalation, and intermediate modes including full exhalation, a partial exhalation while inhibiting further inhalation or exhalation, a partial inhalation while inhibiting further inhalation or exhalation, and a full inhalation;

determining from the comparison, a mode of respiration evident from the acquired ultrasound image;

determining a quality of the acquired ultrasound image;

identifying a change in the determined mode of respiration correlated with an improvement in quality of ultrasound imagery of the target organ; and, presenting the change in the determined mode in the ultrasound imaging device.

12. The computer program product of claim 11, wherein the data store of associations is a deep neural network trained to associate different ones of the modes of respiration with corresponding ones of the previously acquired ultrasound imagery of the different images of the target organ.

13. The computer program product of claim 11, wherein the data store of associations is a table associating individual ones of the different images to corresponding ones of the modes of respiration.

14. The computer program product of claim 11, wherein the method further includes:

determining a prospective disease from the acquired ultrasound image;

identifying a change in the determined mode of respiration correlated with an improvement in quality of ultrasound imagery of the target organ for diagnosing the prospective disease; and, presenting the change in the determined mode in the ultrasound image acquisition device.

15. The computer program product of claim 11, wherein the determination is based upon the comparison attributes of the acquired ultrasound image and not upon an external physiological signal input providing data regarding respiration.

* * * * *